(12) United States Patent
Baek et al.

(10) Patent No.: US 12,731,249 B2
(45) Date of Patent: Sep. 8, 2026

(54) IMAGE PROCESSING METHOD AND IMAGE PROCESSING APPARATUS USING SAME

(71) Applicant: MEDIT CORP., Seoul (KR)

(72) Inventors: Jong Woong Baek, Seoul (KR); Young Mok Cho, Seoul (KR)

(73) Assignee: MEDIT CORP., Seoul (KR)

( * ) Notice: Subject to any disclaimer, the term of this patent is extended or adjusted under 35 U.S.C. 154(b) by 194 days.

(21) Appl. No.: 18/033,171

(22) PCT Filed: Oct. 7, 2021

(86) PCT No.: PCT/KR2021/013800
§ 371 (c)(1),
(2) Date: Apr. 21, 2023

(87) PCT Pub. No.: WO2022/086001
PCT Pub. Date: Apr. 28, 2022

(65) Prior Publication Data
US 2023/0401698 A1 Dec. 14, 2023

(30) Foreign Application Priority Data
Oct. 22, 2020 (KR) ........................ 10-2020-0137425

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0062* (2013.01); *A61B 5/0088* (2013.01);
(Continued)

(58) Field of Classification Search
CPC . G06T 7/0012; G06T 7/11; G06T 7/90; G06T 17/00; G06T 2207/30036;
(Continued)

(56) References Cited

U.S. PATENT DOCUMENTS

2009/0185712 A1 7/2009 Wong et al.
2010/0227296 A1 9/2010 Mandelis et al.
(Continued)

FOREIGN PATENT DOCUMENTS

CN 104574411 A 4/2015
CN 104780830 A 7/2015
(Continued)

OTHER PUBLICATIONS

Korean Office Action dated Dec. 13, 2021 in Application No. 10-2020-0137425.
(Continued)

*Primary Examiner* — Kee M Tung
*Assistant Examiner* — Khoa Vu
(74) *Attorney, Agent, or Firm* — Sughrue Mion, PLLC

(57) ABSTRACT

An image processing method according to the present invention includes a scan step of obtaining image data by scanning an object including teeth, a step of determining caries of the teeth from the image data, and a step of displaying the image data in which the caries has been determined.

20 Claims, 12 Drawing Sheets

(51) Int. Cl.

| | |
|---|---|
| ***G06T 7/11*** | (2017.01) |
| ***G06T 7/90*** | (2017.01) |
| ***G06T 17/00*** | (2006.01) |

(52) U.S. Cl.

CPC .................. *G06T 7/11* (2017.01); *G06T 7/90* (2017.01); *G06T 17/00* (2013.01); *G06T 2207/30036* (2013.01); *G06T 2210/41* (2013.01)

(58) Field of Classification Search

CPC ....... G06T 2210/41; G06T 2207/10024; G06T 2207/10052; G06T 2207/20021; G06T 2207/20084; G06T 2219/2012; G06T 19/20; A61B 5/0062; A61B 5/0088; A61B 1/000094; A61B 1/00172; A61B 1/24; A61B 5/4547; A61B 5/0033; A61B 5/7264; A61B 5/7445; G16H 30/40; G16H 30/20; G16H 40/67; G16H 50/20

See application file for complete search history.

(56) References Cited

U.S. PATENT DOCUMENTS

| | | | | |
|---|---|---|---|---|
| 2010/0322490 | A1 | 12/2010 | Pan et al. | |
| 2011/0275034 | A1* | 11/2011 | Wang | G06T 7/0012 433/215 |
| 2014/0314291 | A1 | 10/2014 | Souza et al. | |
| 2015/0029309 | A1 | 1/2015 | Michaeli et al. | |
| 2015/0164335 | A1 | 6/2015 | Van Der Poel et al. | |
| 2016/0307323 | A1 | 10/2016 | Wu et al. | |
| 2018/0028063 | A1 | 2/2018 | Elbaz et al. | |
| 2018/0028064 | A1 | 2/2018 | Elbaz et al. | |
| 2019/0029522 | A1 | 1/2019 | Sato et al. | |
| 2019/0258690 | A1* | 8/2019 | Elbaz | H04N 13/246 |
| 2021/0241885 | A1* | 8/2021 | Ouyang | G16H 50/20 |
| 2022/0148263 | A1* | 5/2022 | Vannahme | G06T 7/11 |
| 2023/0419631 | A1* | 12/2023 | Ezhov | G16H 50/20 |

FOREIGN PATENT DOCUMENTS

| | | | |
|---|---|---|---|
| CN | 104794688 | A | 7/2015 |
| CN | 106898013 | A | 6/2017 |
| CN | 108460762 | A | 8/2018 |
| CN | 110996836 | A | 4/2020 |
| EP | 2587452 | A1 | 5/2013 |
| JP | 2009-148337 | A | 7/2009 |
| KR | 10-1542867 | B1 | 8/2015 |
| KR | 10-1574376 | B1 | 12/2015 |
| KR | 10-2017-0098386 | A | 8/2017 |
| KR | 10-2018-0045551 | A | 5/2018 |
| KR | 10-2020-0014624 | A | 2/2020 |
| KR | 10-2020-0050346 | A | 5/2020 |
| WO | 2020/182880 | A1 | 9/2020 |

OTHER PUBLICATIONS

Mark Nixon et al.,"8.2.3 Superpixels" in "Feature Extraction and Image Processing for Computer Vision" Nov. 17, 2019, Elsevier pp. 407-411 (5 pages).

K. Moutselos, et al., "Recognizing Occlusal Caries in Dental Intraoral Images Using Deep Learning", Jul. 23, 2019, 41st Annual International Conference of the IEEE Engineering in Medicine and Biology Society, pp. 1617-1620 (4 pages).

Konstantinos Moutselos et al., "Superpixel-Based Classification of Occlusal Caries Photography" 2018 25th IEEE International conference on Image Processing, IEEE, Oct. 7, 2018, pp. 1343-1347 (5 pages).

Extended European Search Report dated Aug. 5, 2024 in Application No. 21883072.7.

International Search Report for PCT/KR2021/013800 dated Jan. 11, 2022.

Chinese Office Action dated May 30, 2025, in Chinese application No. 202180078777.8.

* cited by examiner

Start
Scanning object
S110
Analyzing image data
S130
Three-dimensionally displaying analysis result
S150
End Start
130
Dividing image data into at least one region
S131
Determining caries
S132
Generating three-dimensional model
S133
End Start
Scanning object
S210
Analyzing image data
S230
Three-dimensionally displaying analysis result
S250
End

IMAGE PROCESSING METHOD AND IMAGE PROCESSING APPARATUS USING SAME

CROSS REFERENCE TO RELATED APPLICATIONS

This application is a National Stage of International Application No. PCT/KR2021/013800 filed Oct. 7, 2021, claiming priority based on Korean Patent Application No. 10-2020-0137425 filed Oct. 22, 2020, the entire disclosures of which are incorporated herein by reference.

TECHNICAL FIELD

The present disclosure relates to an image processing method and an image processing apparatus using the same.

BACKGROUND

Dental caries account for a high percentage of dental care. The treatment of a carious tooth is performed by removing a carious part and filling the removed part with amalgam, resin, or gold.

A dentist checks the dental condition of a patient and proposes a treatment method suitable for the dental condition of the patient. However, in general, the dentist checks the dental condition of the patient with the naked eye, and thus depends mainly on his or her subjective judgment. These judgments may vary depending on treatment situation, and inaccurate judgments may be made.

Three-dimensional scanning technology is used in various industries such as measurement, inspection, reverse engineering, content generation, CAD/CAM, and medical devices, and the practicality thereof is further expanding due to the improvement of scanning performance according to the development of computing technology. In particular, in the dental field requiring precise measurements, the frequency of using three-dimensional scanning technology is increasing. In the field of dental industry, there is an industrial demand for a method for diagnosing dental conditions including the presence or absence of caries by using a three-dimensional scanning technology.

In Korean Patent Registration No. 1574376, a light-emitting means is used to detect dental caries. The light-emitting means may generally use fluorescent light, and a scanner, etc. should include a light-emitting means in order to emit fluorescent light to teeth. A scanner including a light-emitting means is relatively heavy and has a high cost, compared with a scanner that does not include a light-emitting means. Therefore, there is a need for a method and a system capable of expressing whether a tooth has caries and the caries state without having a separate light-emitting means.

SUMMARY

The present disclosure provides an image processing method capable of preventing a dentist from performing an unnecessary process to check a patient's dental condition and capable of visually expressing a carious part of a tooth through a scan.

In addition, the present disclosure provides an image processing apparatus capable of visually expressing a carious part of a tooth by performing a series of processes for using the above image processing method.

Technical tasks to be achieved by the present disclosure are not limited to the above-described technical tasks and other technical tasks, which are not described above, may be clearly understood by those skilled in the art from the descriptions below.

In order to achieve the above aspects, the image processing method according to the present disclosure may include a scan step of acquiring image data by scanning an object including a tooth, a data analysis step of determining caries in the image data acquired from the scan step, and a display step of three-dimensionally displaying a caries analysis result.

The image processing apparatus according to the present disclosure may have various elements including a scan unit configured to acquire image data by scanning an object including a tooth, a control unit configured to determine dental caries in the image data to analyze the data, and a display unit configured to three-dimensionally display the image data in which the caries has been determined.

There is an advantage in that a process for determining the state of caries of each tooth is quickly performed by using the image processing method and the image processing apparatus according to the present disclosure.

In addition, by using the image processing method and the image processing apparatus according to the present disclosure, a user (a treating person) can easily determine a carious tooth without using a separate light-emitting means. This results in an advantage of reducing the weight of the apparatus and reducing costs In addition, since image data is generated as a three-dimensional model and a voxel corresponding to a caries region is visually displayed, the user can easily identify how much dental caries has occurred in a clear position inside the oral cavity of a patient. Therefore, the user can suggest a treatment method suitable for the state of a predetermined tooth without checking an actual tooth again.

Figure 1:
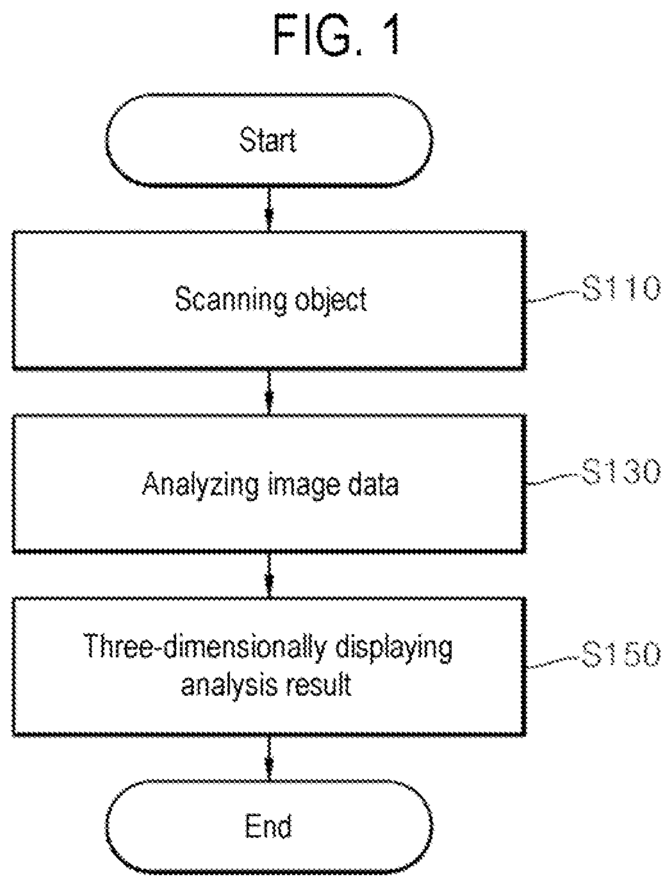
FIG. 1 is a flowchart of an image processing method according to the present disclosure.

| [Description of the Symbols] | |
|---|---|
| S110: Scan step | S130: Data analysis step |
| S131: Step of dividing into large regions | S132: Caries determination step |
| S133: Three-dimensional model generation step | |
| S1311: Step of generating multiple large regions | |
| S1312: Step of comparing characteristic values | |
| S1313: Large region boundary adjustment step | |
| S1321: Caries classification step | |
| S1322: Mask generation step | |
| S1323: Caries expression value mapping step | |
| S150: Display step | |
| S210: Scan step | S230: Data analysis step |
| S231: Three-dimensional model generation step | S232: Tooth-specific segmentation step |
| S233: Step of analyzing image data of selected tooth | |
| S250: Display step | |
| 10: Image processing apparatus | |
| 100: Scan unit | 200: Control unit |
| 210: Large region generation/adjustment unit | 220: Caries determination unit |
| 230: Mask generation unit | 240: Three-dimension model generation unit |
| 300: Display unit | |

DETAILED DESCRIPTION

Hereinafter, some embodiments of the present disclosure will be described in detail with reference to the accompanying drawings. In adding reference numerals to elements in each drawing, the same elements will be designated by the same reference numerals, if possible, although they are shown in different drawings. Further, in the following description of embodiments of the present disclosure, a detailed description of known functions and configurations incorporated herein will be omitted when it is determined that the detailed description may impede the understanding of the embodiments of the present disclosure.

Terms, such as first, second, A, B, (a), (b), or the like may be used herein when describing elements of embodiments of the present disclosure. These terms are merely used to distinguish one element from other elements, and a property, an order, a sequence, and the like of a corresponding element are not limited by the terms. All terms used herein, including technical or scientific terms, have meanings that are generally understood by those skilled in the art to which the present disclosure pertains, unless otherwise defined. Such terms as those defined in a generally used dictionary should be interpreted to have the meanings coinciding with the contextual meanings in the relevant field of art, and are not to be interpreted to have ideal or excessively formal meanings unless clearly defined in the present application.

In describing the present disclosure, a pixel, which is the minimum unit constituting image data, is referred to as a small region, and a superpixel, which is a set of predetermined pixels, is referred to as a large region.

Figure 2:
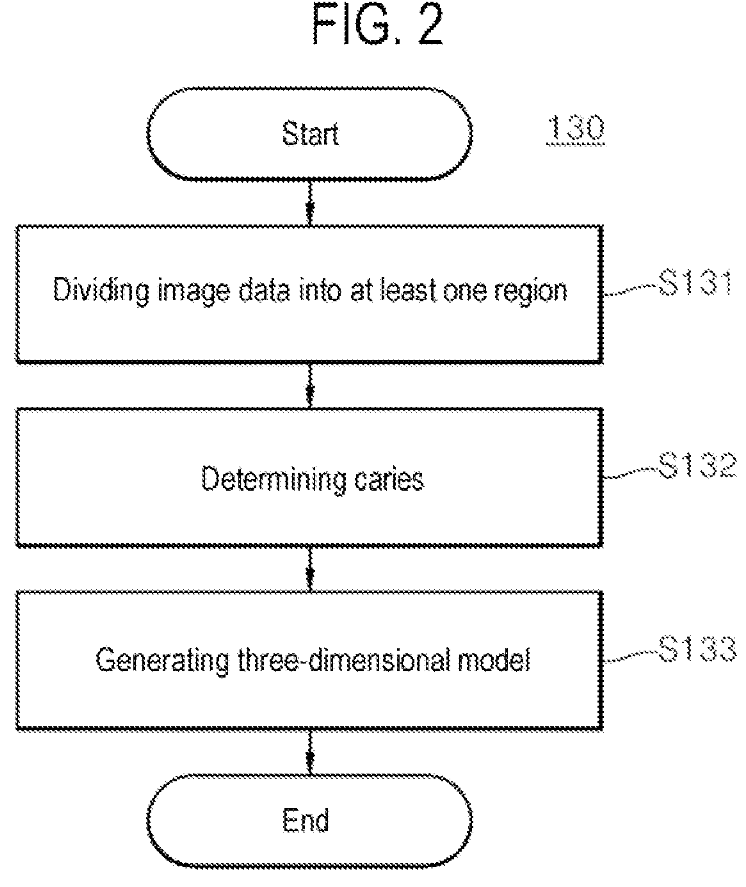
FIGS. 2 to 4 are detailed flowcharts of an image processing method according to the present disclosure.
Figure 3:
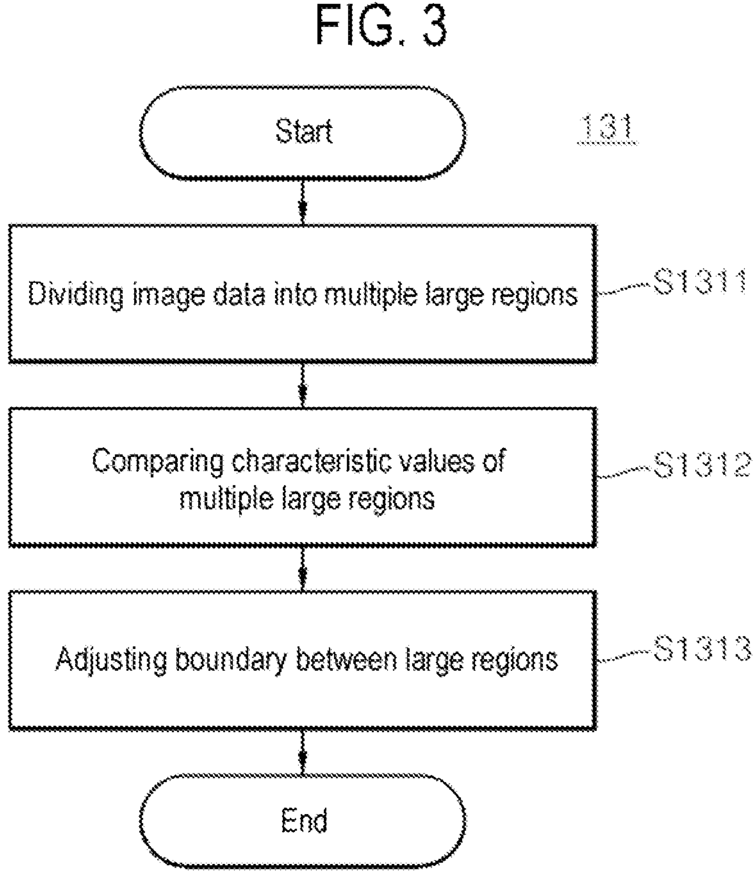
Figure 4:
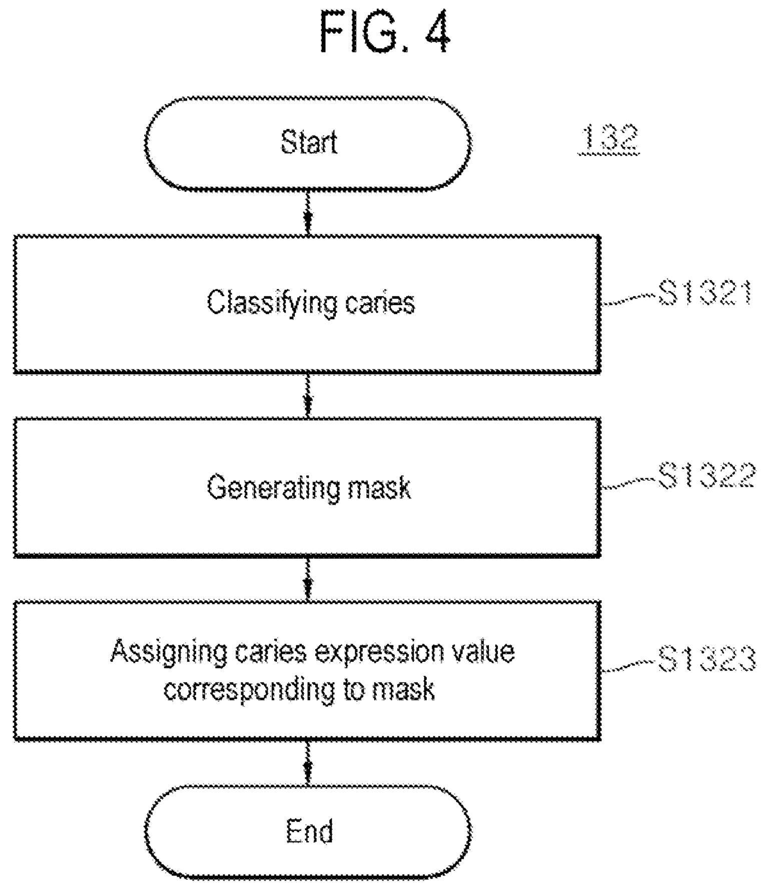

FIG. 1 is a flowchart of an image processing method according to the present disclosure and FIGS. 2 to 4 are detailed flowcharts of an image processing method according to the present disclosure.

Referring to FIG. 1, the image processing method according to the present disclosure may include a scan step S110 of acquiring image data by scanning an object including a tooth, a data analysis step S130 of determining dental caries in the image data, and a display step S150 of three-dimensionally displaying the image data in which the caries has been determined. Hereinafter, each step will be described in detail.

Scan Step S110

The image processing method according to the present disclosure includes the scan step S110. The scan step S110 may be a step of acquiring image data by scanning an object. The object may be various objects but, when considering the purpose of the present disclosure, may be the inside of a patient's oral cavity including the teeth, the gingiva (gum), the dental arch, etc. The scan step S110 is performed by a scan unit of an image processing apparatus which will be described later, and the scan unit may be a handheld scanner capable of freely adjusting a scan distance to and a scan angle with an object.

The image data may be a shot of two-dimensional image data or three-dimensional image data. The image data acquired in the scan step S110 may be used in the analysis step S130 which will be described later.

In an embodiment, the scan step S110 may mean photographing an object, and in this case, image data may be two-dimensional image data. More specifically, in the present disclosure, at the time of caries determination, the two-dimensional image is divided into large regions having similar characteristic values, and caries is determined from the large regions. Compared with acquiring and analyzing characteristic values from three-dimensional data, this has advantages of saving storage space, enabling rapid analysis, and preventing waste of resources.

The scan unit may emit light to the object in order to generate a three-dimensional model from the acquired image data. At this time, the light emitted toward the object may have various forms. As an example, the light may be light having a wavelength in a visible light region. Also, the light may be structured light having a predetermined pattern. The structured light allows image data to have depth information and, as an example, a stripe pattern in which straight lines of different colors appear continuously may be used as structured light. For example, the structured light may be light having a vertical stripe pattern or a horizontal stripe pattern in which bright parts having relatively high brightness and dark parts having relatively low brightness are alternately disposed. The pattern of structured light may be generated through a pattern generation means such as a pattern mask or a digital micromirror device (DMD). However, it is not always necessary to use structured light to acquire a three-dimensional model, and any method capable of acquiring depth information of an object to acquire a three-dimensional model can be used.

Data Analysis Step S130

Subsequently, the data analysis step S130 of determining dental caries through the image data acquired in the scan step S110 described above may be performed. Referring to FIG. 2, the data analysis step S130 may include a step S131 of dividing the image data into predetermined large regions, a step S132 of determining dental caries from the image data, and a step S133 of generating a three-dimensional model from the image data from which the caries has been determined. That is, the data analysis step S130 includes processes of interpreting and processing the image data acquired in the scan step S110.

Hereinafter, detailed steps of the data analysis step S130 will be described.

Referring to FIG. 2, the data analysis step S130 may include the step S131 of dividing image data into at least one large region. In reality, there may be multiple large regions, and a boundary exists between the large regions. In this case, each of the large regions may be a superpixel including at least one small region.

Dividing the image data into the at least one large region is for the purpose of determining caries in the large region, and through this process as a result may reduce the computational load of an apparatus performing the image processing method according to the present disclosure.

FIGS. 3 and 5 to 8 illustrate a process of generating and adjusting large regions in an image processing method according to the present disclosure.

Figure 5:
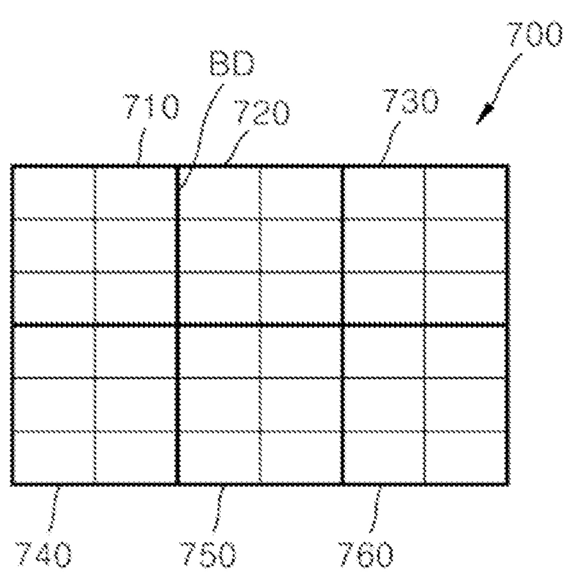
FIGS. 5 to 8 illustrate a process of generating and adjusting large regions in an image processing method according to the present disclosure.

Referring to FIGS. 3 and 5, the step S131 of dividing into large regions includes a step S1311 of generating multiple large regions for dividing image data. As an example, the image data is acquired in the form of a rectangle, and the image data is formed of a set of small regions that are the minimum units for expressing an image.

The image data may be formed by a collection of M×N (M and N are natural numbers, and M×N may imply the number of pixels arranged in the horizontal direction×the number of small regions arranged in the vertical direction) small regions in a regular arrangement. At this time, in the step S1311 of generating multiple large regions, the image data may be divided to generate large regions having the same size and including the same number of small regions. For example, when image data has a resolution of 1600×1200 small regions, 16 large regions, each of which has 400×300 small regions, may be generated to divide the image data. When the image data is divided into the multiple large regions, a step S1312 of comparing characteristic values and a step S1313 of adjusting a boundary, which will be described later, may be quickly performed.

In the step S1311 of generating the multiple large regions, the number of large regions may be appropriately preconfigured according to the resolution of image data. As an example, the image data has a resolution of 1600×1200 small regions as a whole, and the image data may be divided to generate 10 preconfigured large regions. At this time, according to the number of large regions, the image data may be divided into large regions, each of which has a resolution of 320×600 small regions.

As an example for describing the present disclosure, image data having 6×6 small regions is presented. The image data may be divided into six large regions, each of which has the same size and 2×3 small regions, in order to be divided into multiple large regions 710, 720, 730, 740, 750, and 760. Boundaries BD between the large regions 710, 720, 730, 740, 750, and 760 may be optionally configured, and the boundaries BD may be changed by the boundary adjusting step S1313 which will be described later.

The number of the large regions and the size of the large regions, described above, are examples, and may be variably configured depending on to a user's needs or conditions of image data.

In order to adjust the boundaries, the step S131 of dividing into large regions includes the step S1312 of comparing characteristic values between the multiple large regions. The step S1312 of comparing characteristic values is a process for grouping small regions having identical or similar characteristics into large regions. The characteristic values may be at least one of pieces of information obtained from the image data. As an example, the characteristic values may include color information, size information, texture information, and fill information indicating the difference between boundary boxes of data that has been input into small regions constituting the image data. At this time, for the purpose of the present disclosure for determining caries, color information may be used as the characteristic values. In the step S1312 of comparing characteristic values, characteristic values of small regions adjacent to the boundaries BD of the large regions may be compared. By comparing the characteristic values of the small regions adjacent to the boundaries BD, the boundaries BD may be changed (S1313) so that small regions having similar characteristic values form a large region.

Figure 6:
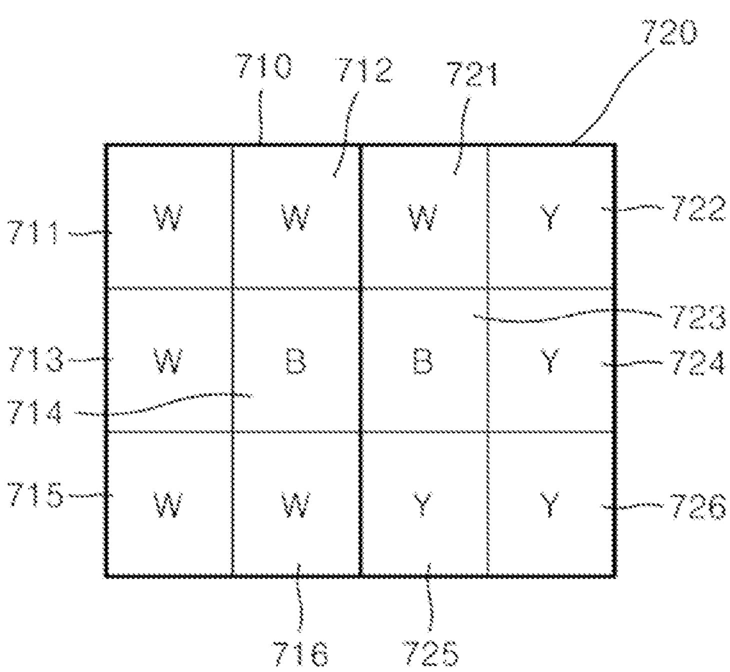
Figure 7:
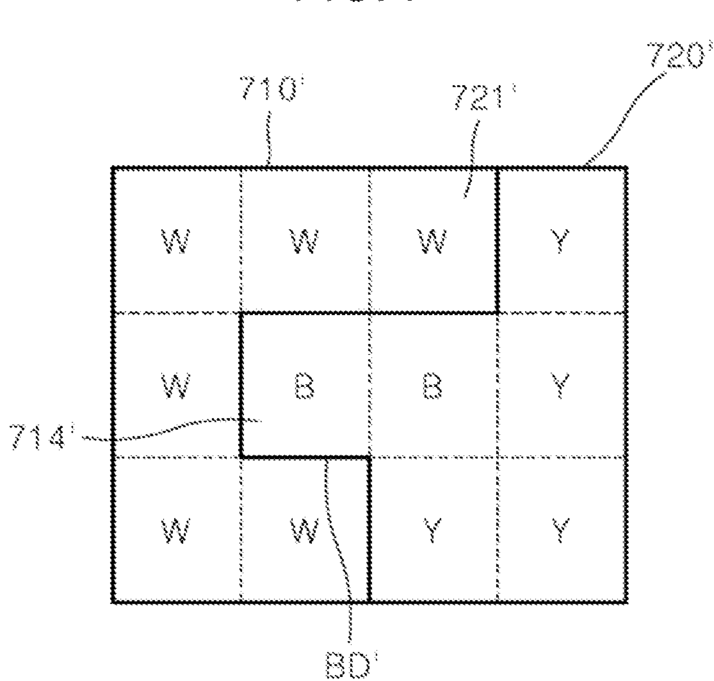
Figure 8:
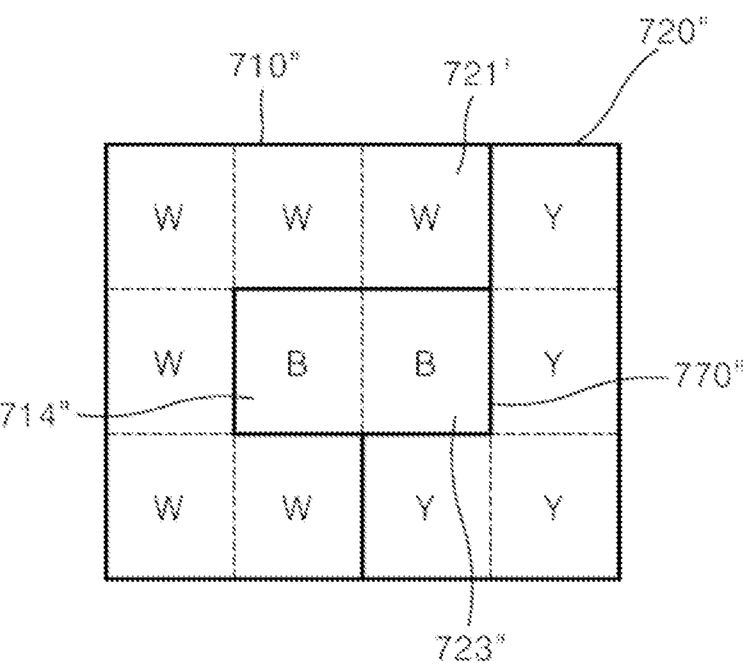

Referring to FIGS. 6 to 8, image data divided into large regions acquires color information of pixels 711 to 716 and 721 to 726 corresponding to respective small regions. At this time, the color information may be acquired through various color models such as a Gray model, an RGB model, an HSV model, a CMYK model, and a YCbCr model. However, the Gray model expresses an achromatic color of 0 to 255, and it is not easy to clearly compare characteristic values and determine actual caries. Accordingly, a color model used may be a chromatic color model. In order to determine similarity between small regions, a color histogram of a corresponding color model may be used as a characteristic value.

The similarity determination based on the color histogram will be described in more detail. A color histogram of each small region may be generated, and similarity may be determined by overlapping color histograms of adjacent small regions having a boundary BD interposed therebetween. As an example, when a color histogram is generated for each of a random first small region and a random second small region (not shown) adjacent to each other with a boundary interposed therebetween, and when the generated color histograms are overlapped, an overlapping area may be calculated. When the overlapping area has a value equal to or greater than a threshold value, it may be determined that the first small region and the second small region have similar characteristic values.

Hereinafter, for convenience of description, one small region will be described as having a representative color. However, this should be interpreted as describing that one small region has a color histogram including a representative color.

Referring to FIG. 6, a characteristic value is assigned to each small region. At this time, characteristic values of small regions adjacent to a boundary between large regions may be compared with each other. For example, characteristic values of a second small region 712 of a first large region 710 and a first small region 721 of a second large region 720 may be compared with each other. As shown, both the characteristic value of the second small region 712 of the first large region 710 and the characteristic value of the first small region 721 of the second large region 720 may be W (white).

In addition, a characteristic value of a fourth small region 714 of the first large region 710 and a characteristic value of a third small region 723 of the second large region 720 may be compared with each other. As shown, both characteristic value of the fourth small region 714 of the first large region 710 and the characteristic value of the third small region 723 of the second large region 720 may be B (black).

Similarly, a characteristic value of a sixth small region 716 of the first large region 710 and a characteristic value of a fifth small region 725 of the second large region 720 may be compared with each other. As shown, the characteristic value of the sixth small region 716 of the first large region 710 may be W (white), and the characteristic value of the fifth small region 725 of the second large region 720 may be Y (yellow).

According to the comparison of characteristic values of small regions adjacent to a boundary BD, the boundary BD may be adjusted to a new boundary BD' (S1313). Referring to FIG. 7, a portion that was the first small region 721 of the second large region 720 may be incorporated into the first large region 710 and correspond to a seventh small region 721' of the first large region 710. Also, a portion that was the fourth small region 714 of the first large region 710 may be incorporated into the second large region 720 and correspond to a seventh small region 714' of the second large region 720. Accordingly, the boundary BD' may be adjusted according to a change in the large regions to which the small regions belong. Small region adjustment may be performed by referring to characteristic values of other small regions adjacent to small regions adjacent to the existing boundary BD. According to the continuous renewal of the boundary BD in the image data, small regions having similar characteristic values may form a large region.

Referring to FIG. 8, the number of large regions may be changed depending on image data, and accordingly, the number of small regions included in initial large regions may also be changed. More specifically, the number of large regions may be greater or smaller than the number of initially generated large regions according to the distribution of characteristic values of small regions. For example, the fourth small region 714 included in the first large region 710 and the third small region 723 included in the second large region 720 may form one new large region. A new large region 770" may include small regions 714" and 723" having characteristic values of B (black). In this way, small regions having similar characteristic values may form a large region, and thus image data may be divided in the form of superpixels. Accordingly, whether a tooth has caries may be determined for each large region, and the user can quickly identify a tooth with caries. In addition, caries teeth may be determined for each large region, thereby reducing the computational load of an apparatus performing the image processing method according to the present disclosure.

Figure 9A:
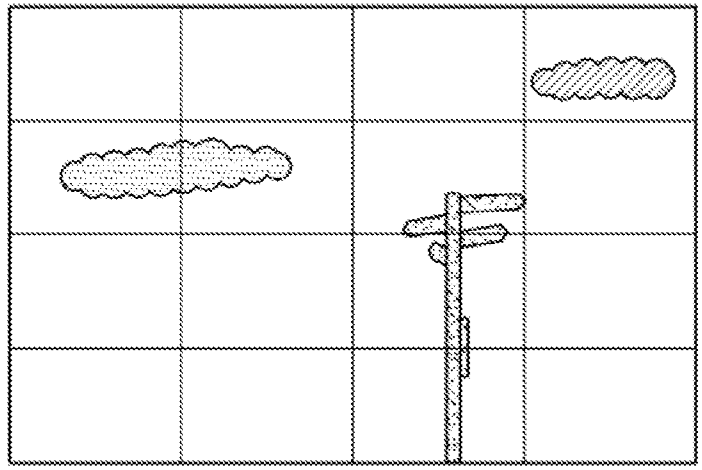
FIG. 9A, FIG. 9B and FIG. 9C illustrate exemplary image data in which a large region is adjusted by an image processing method according to the present disclosure.
Figure 9B:
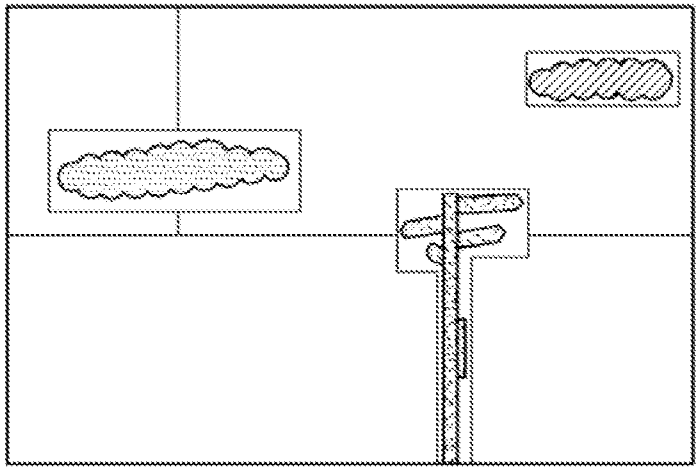
Figure 9C:
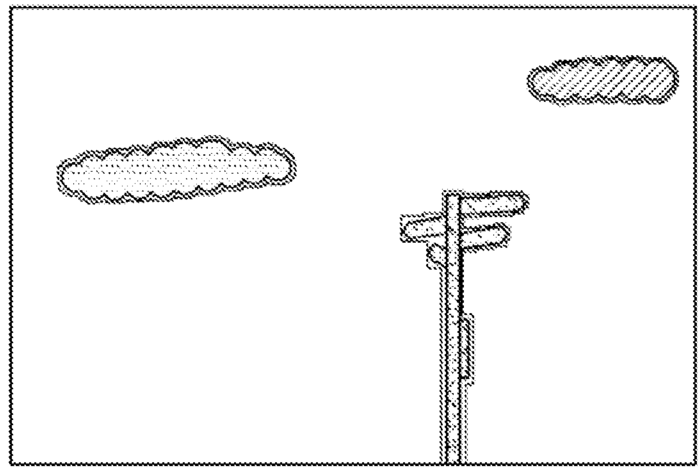

FIGS. 9A, 9B and 9C illustrate exemplary image data in which a large region is adjusted by an image processing method according to the present disclosure.

As shown in FIGS. 9A to 9C, a region of image data is adjusted according to a characteristic value (e.g., color information). First, in FIG. 9A, large regions having the same size are generated to divide image data. In FIG. 9B, characteristic value comparison is performed near boundaries between adjacent large regions, and boundary adjustment is performed so that small regions having similar characteristic values form a large region. Some large regions may be newly created or merged by performing the boundary adjustment. In FIG. 9C, the boundary adjustment is completed, and a milestone, a first cloud, a second cloud, and a background are distinguished precisely enough to be recognized.

Hereinafter, the caries determination step S132 will be described in detail with reference to related drawings.

Referring to FIG. 4, the caries determination step S132 includes a caries classification step S1321 of determining whether caries is present for each large region or determining a caries class for a region determined to have caries. Specifically, in the caries classification step S1321, caries features and/or the degree of caries severity in image data divided into large regions may be extracted using artificial intelligence (AI).

The artificial intelligence may be deep learning, and specifically, at least one selected from among Artificial Neural Network (ANN), Convolution Neural Network (CNN), Deep Neural Network (DNN), and Recurrent Neural Network (RNN).

In the present disclosure, for example, the Convolution Neural Network (CNN) may be used. In the CNN, a convolution layer and a pooling layer are performed in order, or a fully connected layer may be additionally performed in addition to the convolution layer and the pooling layer.

More specifically, the CNN acquires a feature map through a convolution layer that performs a convolution step by using a kernel filter having a size of n×n. Thereafter, a pooling layer highlights a caries feature of the feature map by sampling a value of the feature map using the kernel filter having a size of n×n. The caries feature may be extracted by repeatedly performing the above process, and optionally, a fully connected layer may classify caries classes (i.e., an indicator indicating the severity of caries) according to a preconfigured criteria.

The preconfigured criteria may be, for example, the International Caries Detection and Assessment System (ICDAS). ICDAS is criteria by which the severity of caries is classified into levels, and the severity of caries are divided into seven levels of integer numbers from 0 to 6. The level may be determined by a characteristic value of a large region.

After the caries classes are classified, in the caries determination step S132, a mask including at least one mask region may be generated based on the caries classes and/or the determined presence or absence of caries (S1322). The mask may be a set of portions which has been determined to have caries based on the presence or absence of caries and/or the caries class, and the portions may be large regions. That is, large regions determined to have caries may constitute the mask region included in the mask.

Thereafter, caries expression values corresponding to the presence or absence of caries and/or the caries classes may be mapped to the mask region (S1323). The mapping of the caries expression values may mean allocation of a specific expression values to the mask region. The caries expression values may be a means capable of visually displaying the presence or absence of dental caries to the user in the display step. As an example, the caries expression values may be at least one of a predetermined color and a predetermined pattern. The mask to which the caries expression values are mapped may overlap the image data, and may be displayed together when displaying the image data or the three-dimensional model.

The caries expression values may be mapped based on the presence or absence of caries and/or the caries class. As an example, a portion determined not to have caries in the caries classification step S1321 is not formed as a mask, and a portion determined to have caries is formed as a mask.

Therefore, only the presence or absence of caries may be visually displayed by mapping at least one of the predetermined color and the predetermined pattern with respect to the entire mask. That is, the caries expression values may be the same value regardless of the caries classes. For example, in relation to caries expression values, according to the result of determining only the presence or absence of caries without classifying caries classes, the same caries expression value may be applied to portions in which caries has occurred, or the same caries expression value may be applied to mask regions having caries classes 3 to 6. The caries expression values may be a fluorescent color, a red color, or a black color. As the caries expression values are displayed, the user can easily identify a tooth on which caries has occurred.

Alternatively, the caries expression values may be mapped to be different values according to caries classes. More specifically, the mask may include a mask region formed for each caries class, and different colors may be mapped to caries classes of the mask regions.

Caries class classification and caries expression value mapping will be described in more detail. As an example, large regions may have various characteristic values such as white, yellow, brown, and black. One large region may include small regions having identical or similar characteristic values. Caries features and/or caries classes may be extracted from the characteristic values of the large region by using artificial intelligence, and a mask may be generated based on the extracted values. The generated mask may include at least one mask region, and a caries expression value may be mapped to the mask region.

For example, when a characteristic value is white in a random large region according to preconfigured criteria, the region is determined to be a portion where caries has not occurred (level 0) and is not formed as a mask. In addition, when a portion having a characteristic value of yellow is located on dry enamel, the portion is determined to be a portion where slight caries has occurred (level 1), and a caries expression value may be mapped to a mask region corresponding to the caries region. In addition, when a portion having a characteristic value of yellow is located on wet enamel, the portion is determined to be a portion where normal caries has occurred (level 2), and a caries expression value may be mapped to a mask region corresponding to the caries region.

In addition, when a cavity occurs in a tooth, it is determined that the region is a portion in which caries of levels 3 to 6 has occurred based on the area and/or ratio of the cavity, and a caries expression value may be mapped to a mask region corresponding to the caries region. More specifically, levels of 3 to 6 according to the cavity may be determined based on the occupation ratio of a large region having a characteristic value of black or the area of the large region having a characteristic value of black. Alternatively, the caries classes may be classified by mixing the relationship between the ratio and the area.

For example, in a large region having a characteristic value of black and a size of less than 0.5 mm in a portion corresponding to enamel, a caries expression value may be mapped to a mask region corresponding to the caries region. Similarly, when a large region having a characteristic value of black occupies more than half of predetermined image data, it is determined that very severe caries has occurred, and a caries expression value may be mapped to a mask region corresponding to the caries region. According to the above process, it is possible to indicate a portion in which caries has occurred. However, the reference numerical values for classifying caries classes have been used as an example to describe the present disclosure. Therefore, the numerical values may be changed as needed.

Contents in which caries expression values have different colors depending on caries classes will be described in detail. As an example, when the caries class is level 0, no caries expression value is mapped because a mask in not generated. When the caries class is level 1, green may be mapped to a corresponding mask region, when the caries class is level 2, cyan may be mapped to a corresponding mask region, when the caries class is level 3, magenta may be mapped to a corresponding mask region, when the caries class is level 4, blue may be mapped to a corresponding mask region, when the caries class is level 5, red may be mapped to a corresponding mask region, and when the caries class is level 6, black may be mapped to a corresponding mask region.

A mask to which a caries expression value is mapped as described above may be displayed together with the actual color of the image data while overlapping the image data. The mask may have predetermined transparency. Due to the mask having the predetermined transparency, there is an advantage in that the user may identify both the actual shape of a tooth and whether the tooth is carious.

According to an alternative embodiment, the caries expression values may be 6-level caries class classification criteria including integers from 0 to 5. The criteria may be abbreviated criteria which is the partially simplified ICDAS criteria. As an example, in the criteria, when a characteristic value is white in a random large region, the region is determined to be a portion in which caries has not occurred (level 0), and is not formed as a mask. In addition, when there is a portion having a characteristic value of yellow, the portion is determined to be a portion in which normal caries has occurred (level 1), and a caries expression value may be mapped to a mask region corresponding to the caries region.

In addition, when a cavity has occurred in a tooth, the corresponding region is determined to be a portion in which caries of levels 2 to 5 has occurred according to the area and/or ratio of the cavity, and a caries expression value may be mapped to a mask region corresponding to the caries region. More specifically, levels 2 to 5 according to the cavity may be determined based on the occupation ratio of a large region having a characteristic value of black or the area of the large region having a characteristic value of black. Alternatively, the caries class may be classified by using the relationship between the ratio and the area. As described above, the same or different caries expression values may be mapped according to caries classes.

When the caries determination step S132 is completed and a mask is generated, and when caries expression values are mapped according to the presence or absence of caries and/or the caries classes (S1323), the step S133 of generating a three-dimensional model including at least one voxel from the image data may be performed. In this case, the three-dimensional model may be generated by aligning multiple pieces of image data, and a two-dimensional data may be generated as the three-dimensional model through depth information of the image data. Meanwhile, the mask overlaps the image data. When the three-dimensional model is generated from image data, the voxels constituting the three-dimensional model may display caries expression values only in portions where the caries expression values overlap. Accordingly, the three-dimensional model may display caries regions together through the caries expression values.

Figure 10:
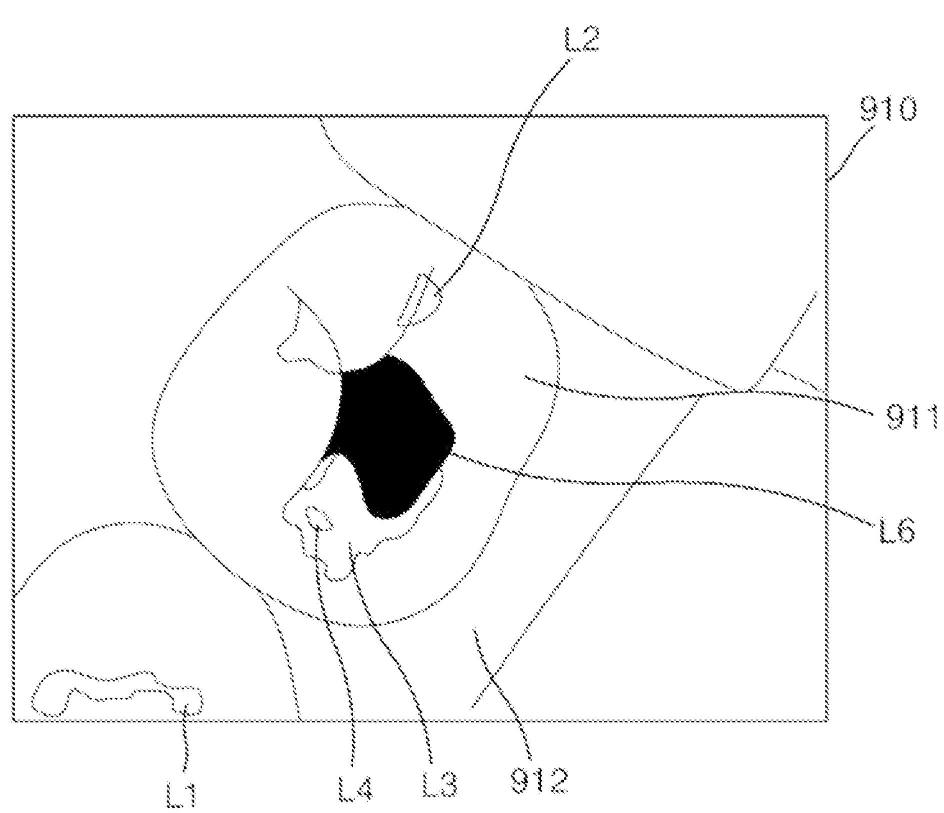
FIG. 10 schematically illustrates image data acquired through a scan step in an image processing method according to the present disclosure.
Figure 11:
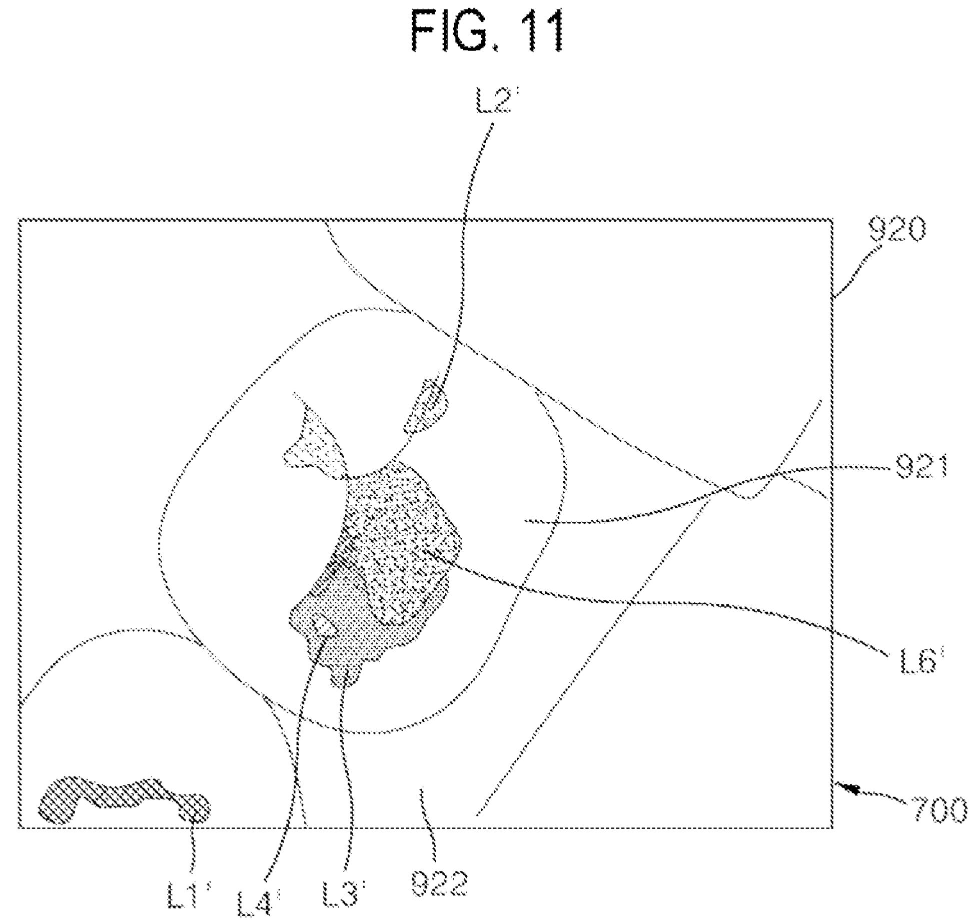
FIG. 11 schematically illustrates image data in which carious tooth determination is performed in an image processing method according to the present disclosure.

FIG. 10 schematically illustrates image data acquired through a scan step in an image processing method according to the present disclosure and FIG. 11 schematically illustrates image data in which carious tooth determination is performed in an image processing method according to the present disclosure.

Referring to FIG. 10, image data 910 acquired through the scan step S110 is illustrated. The image data 910 may include a tooth 911 and a gingiva 912, and portions of the tooth 911, in which caries is in progress, may be identified. As an example, a first carious portion L1, a second carious portion L2, a third carious portion L3, a fourth carious portion L4, and a fifth carious portion L6 may be shown. The carious portions L1, L2, L3, L4, and L6 may be separated into at least one large region into which division is made according to characteristic values in the step S131 of dividing into large regions (S131).

Referring to FIG. 11, after the caries determination is completed, caries expression values may be displayed on image data. Through the caries expression values, the user can clearly recognize locations L1', L2', L3', L4', and L6' in which caries has occurred on the image data 920. Due to the display of the caries expression values, there is an advantage in that the user can precisely recognize whether caries has occurred in a tooth and the severity of the caries, and can perform treatment according to the severity of the caries.

Display Step S150

When the data analysis step S130 is completed, the display step S150 of three-dimensionally displaying image data in which caries has been determined may be performed. In the display step S150, the data analysis result may be displayed through an output device, and the output device may be a visual display device such as a monitor.

Information displayed in the display step S150 is two-dimensional image data of an object including a tooth or a three-dimensional model generated through the three-dimensional model generation step S133. At this time, it may be intuitive to display a caries expression value on the two-dimensional image data, but it is not easy to exactly identify where caries has occurred in the tooth. In contrast, the three-dimensional model expresses the color and shape of an object in a three-dimensional manner. The three-dimensional model may have the same color, shape, dimensions, etc. as an actual object, and the user can easily identify the location, size, and angle of caries, when a caries expression value is displayed on the three-dimensional model and thus may provide an optimal treatment to a patient. Therefore, it is effective to display, on the three-dimensional model, the data (in particular, the caries determination) analyzed in the data analysis step S130.

The above-described image processing method may be performed only on a portion corresponding to a tooth region, and the image processing method according to the present disclosure may not be applied to portions corresponding to the gingiva and a dental arch. As an example, when a color acquired from each small region constituting image data corresponds to red series in a color histogram, an object included in the image data is highly likely to correspond to the gingiva or a dental arch. Accordingly, when it is determined that the object is the gingiva or the dental arch, based on the color obtained from the small region, a mask may not be generated at a corresponding position. Through the above process, a tooth and other portions (the gingiva and the dental arch) in the oral cavity are distinguished, and only with respect to a tooth region, a mask is selectively generated and a caries expression value may be mapped. Accordingly, the presence or absence of caries and/or the caries class may be determined only with respect to the tooth region, and user confusion may be prevented.

In addition, in the above-described image processing method, not only the caries expression value may be displayed over the entire three-dimensional model, but also a segmentation process may be performed with respect to each tooth, and the caries class of each tooth may be classified. Depending on the caries class determined for each tooth, a process of presenting a suitable treatment method based on the location and area of caries that has occurred in a predetermined tooth may be additionally performed. As an example, when caries has occurred in the cusp of a tooth, an onlay treatment method may be displayed together with a caries expression value, and when caries has occurred in a portion other than the cusp of the tooth, an inlay treatment method may be displayed together with a caries expression value.

In the foregoing, externally appearing caries may be determined through characteristic values of image data. However, internal caries that is not externally exposed may need to be determined, and a dental extraction may be required depending on the progress of the internal caries. Therefore, when each tooth for which the segmentation process has been performed in the generated three-dimensional model is selected, a dental extraction-type treatment method according to internal caries may be displayed together with a caries expression value. As an example, when a predetermined tooth is selected, a step of determining internal caries may be additionally performed in addition to the previously performed process of determining tooth surface caries. The step of determining internal caries may be performed based on a characteristic value acquired from image data, and the characteristic value may be, for example, color information. In the case in which a predetermined tooth has a color of low saturation as a whole, the tooth may be determined to have internal caries even when the caries class is low. For example, when a low-saturation portion in image data of the predetermined tooth is more than a preconfigured ratio, the low-saturation portion may be determined to be internal caries, and a "dental extraction" treatment method may be displayed. The internal caries may be determined using color saturation, but may also be determined using sound wave scan information, infrared scan information, etc. Since the internal caries determination step is further included, it is possible to treat not only surface caries but also a potentially carious tooth.

Hereinafter, an image processing method according to another embodiment of the present disclosure will be described. In describing another embodiment of the present disclosure, the same content as that of the image processing method according to the embodiment of the present disclosure will be omitted.

Figure 12:
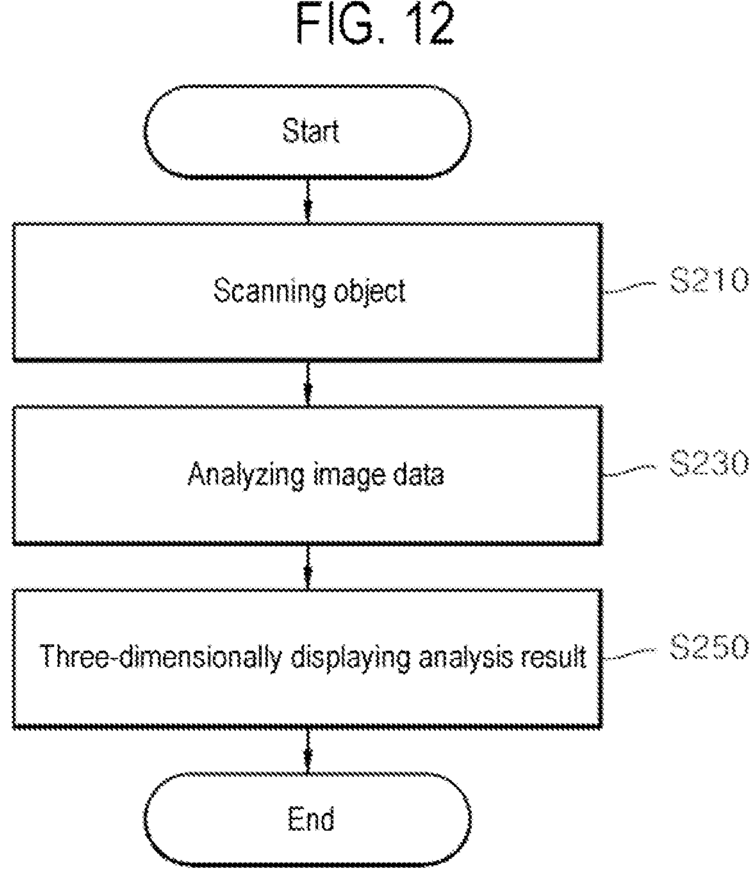
FIG. 12 is a flowchart of an image data processing method according to another embodiment of the present disclosure.
Figure 13:
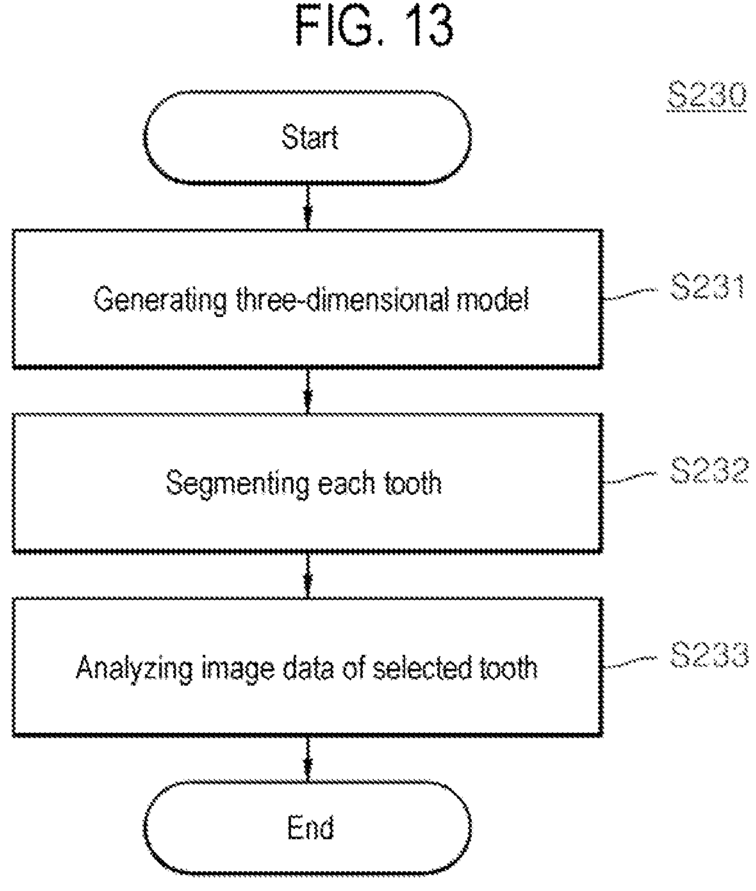
FIG. 13 is a detailed flowchart of an image data processing method according to another embodiment of the present disclosure.

FIG. 12 is a flowchart of an image data processing method according to another embodiment of the present disclosure. FIG. 13 is a detailed flowchart of the image data processing method according to the another embodiment of the present disclosure.

Referring to FIGS. 12 and 13, an image processing method according to another embodiment of the present disclosure includes a scan step S210 of acquiring image data by scanning an object including a tooth, a data analysis step S230 of determining dental caries in the image data, and a step S250 of three-dimensionally displaying the image data in which the caries has been determined. The scan step S210 and the display step S250 according to the other embodiment of the present disclosure are as described above.

In the data analysis step S230, unlike the above, a three-dimensional model may be generated (S231) without determining caries from the image data acquired in the scan step S210.

Subsequently, the image processing method according to the other embodiment of the present disclosure may include a step S232 of classifying the three-dimensional model for each tooth. The three-dimensional model may be classified for each tooth, thereby enabling a user to select only a tooth for which caries determination is desired. More specifically, when the user selects a tooth for which caries determination is desired, only two-dimensional image data including the tooth may be extracted, and caries determination may be performed from the extracted image data (S233). Thus, there is an advantage in that only image data including a tooth to be analyzed may be analyzed, thereby saving system resources required for analysis and enabling rapid analysis.

The caries determination using image data may be performed using the method described above, and thus the related description will be omitted.

Alternatively, when the image data is three-dimensional data, the three-dimensional data may be divided into three-dimensional large regions. At a boundary between the three-dimensional large regions, characteristic values of adjacent three-dimensional small regions may be compared with each other, and the boundary between the three-dimensional large regions may be adjusted according to the comparison of the characteristic values. Accordingly, three-dimensional small regions having similar characteristic values may form a three-dimensional large region.

Thereafter, determination of the presence or absence of caries and/or a caries class may be performed for each three-dimensional large region, and a three-dimensional mask having at least one mask region may be generated. Subsequently, a caries expression value may be mapped to the mask region according to the presence or absence of caries and/or the caries class. This is a change from a two-dimensional flat mask to a three-dimensional stereoscopic mask, and the overall caries determination step is as described above.

In addition, with respect to a portion determined to correspond to a gingiva or a dental arch in the three-dimensional model, a mask may not be formed or a caries expression value may not be mapped. This means that when a characteristic value of a three-dimensional small region (voxel) is a red-series color on a color histogram, a corresponding portion may be determined to be a gingiva or a dental arch. A caries expression value may be prevented from being mapped to the portion determined to be the gingiva or the dental arch, thereby preventing confusion of the user.

Hereinafter, an image processing apparatus according to the present disclosure will be described in detail. However, the content overlapping with that of the above-described image processing method according to the present disclosure will be omitted.

Figure 14:
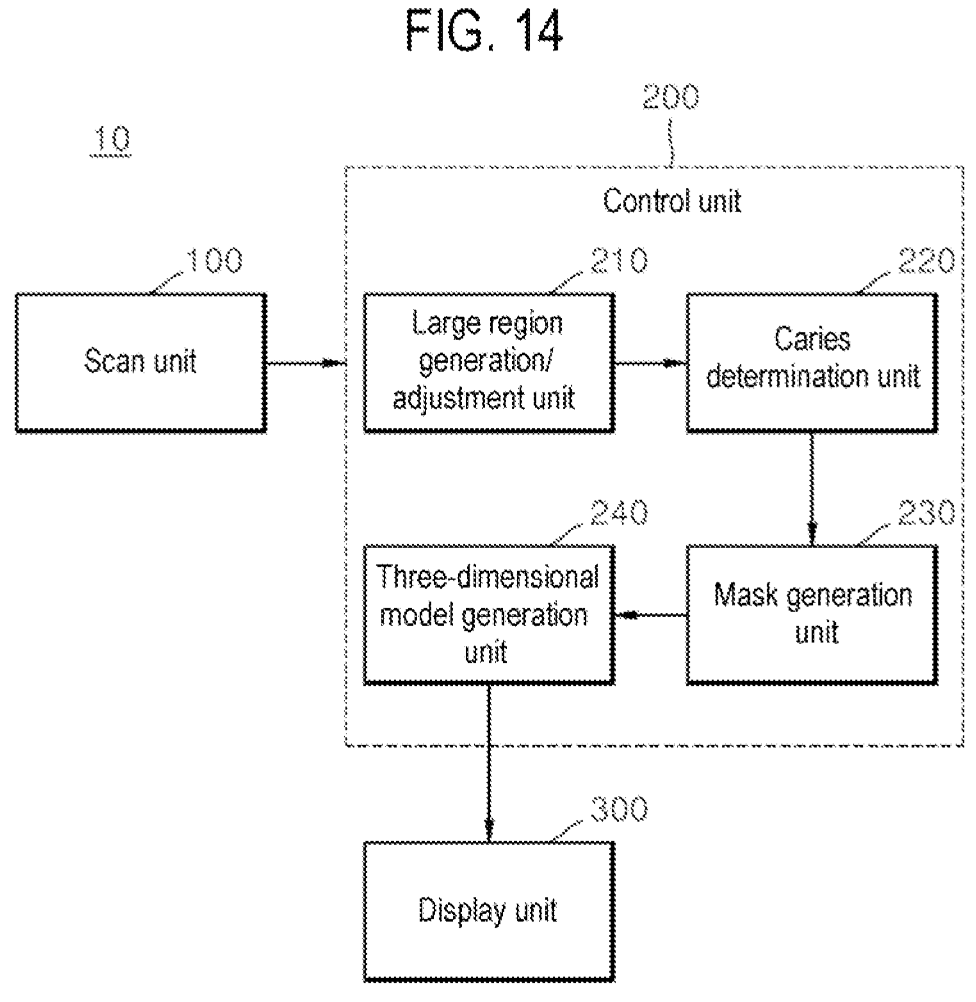
FIG. 14 illustrates a configuration of an image processing apparatus according to the present disclosure.

FIG. 14 illustrates a configuration of an image processing apparatus according to the present disclosure.

Referring to FIG. 14, the image processing apparatus 10 according to the present disclosure includes a scan unit 100 configured to obtain image data by scanning an object including a tooth, a control unit 200 to determine dental caries from the image data by analyzing the data, and a display unit 300 for three-dimensionally displaying the image data from which the caries has been determined.

The scan unit 100 scans an object including a tooth. For the purpose of the present disclosure, the object may be the inside of a patient's oral cavity for determining whether caries has occurred in a tooth. The scan unit 100 may be a three-dimensional scanner capable of scanning the inside of the patient's oral cavity at various scan distances and scan angles while moving into or out of the patient's oral cavity. The scan unit 100 may include at least one camera and an imaging sensor connected thereto so as to acquire image data of an object. The imaging sensor may be a mono image sensor or a color image sensor such as a CCD sensor or a CMOS sensor.

The scan unit 100 may emit structured light having a predetermined pattern so that the control unit 200 generates a three-dimensional model from the acquired image data. The pattern of the structured light may be generated through a pattern generation means such as a pattern mask or a digital micromirror device (DMD). However, in order to generate image data as a three-dimensional model, it is not necessary to use structured light, and at least one of known methods such as a mark, a laser, and TOF may be used.

Hereinafter, a configuration of the control unit 200 will be described in detail.

The control unit 200 may analyze the image data acquired by the scan unit 100. More specifically, the control unit 200 may include a large region generation/adjustment unit 210 that divides image data into at least one large region. In this case, the large region may be a superpixel including at least one small region, and the small region may be a pixel constituting the image data. The large region generation/adjustment unit 210 may generate large regions such that the image data is divided into at least one large region having the same size and the same small regions. A boundary may be formed between the large regions.

The large region generation/adjustment unit 210 may compare characteristic values of small regions adjacent to the boundary. At this time, the characteristic values to be compared are portion-specific features of the image data, which the small regions have, and may include, for example, color information, texture information, size information, fill information, etc., and the characteristic values for the purpose of the present disclosure may be color information acquired from image data.

When the characteristic value comparison is performed, the large region generation/adjustment unit 210 may adjust the boundary so that small regions having similar feature values are formed as the same large region. The process in which the large region generation/adjustment unit 210 generates the large regions, compares the characteristic values, and adjusts the boundary is same as that described above in the image processing method according to the present disclosure.

The control unit 200 may include a caries determination unit 220 for determining caries based on large regions having an adjusted boundary. The caries determination unit 220 may determine the presence or absence of caries through artificial intelligence (AI) technology including deep learning, and a deep learning technology capable of being used to determine caries may be one selected from among ANN, CNN, DNN, and RNN, which have been described above. The caries determination unit 220 may determine caries by determining the presence or absence of caries and/or a caries class for each large region, and the criteria may be ICDAS criteria. However, the present disclosure is not limited to the ICDAS criteria, and appropriate classification criteria may be applied in some cases.

The control unit 200 may further include a mask generation unit 230 for generating a mask having at least one mask region, based on the presence or absence of caries and/or the caries class determined by the caries determination unit 220.

Thereafter, the mask generation unit 230 may map a caries expression value corresponding to the presence or absence of caries and/or the caries class to each mask region of the mask. Mapping the caries expression value may mean assigning a specific expression value to a mask region. The caries expression value may be a means capable of visually displaying the presence or absence of dental caries to the user in the display step. As an example, the caries expression value may be at least one of a predetermined color and a predetermined pattern. The mask to which caries expression values are mapped overlaps the image data, and may be displayed together when displaying the image data or a three-dimensional model to be described later.

The process of determining caries, the process of generating a mask, and the process of mapping caries expression values to the mask are the same as those described above in relation to the image processing method according to the present disclosure, so redundant descriptions will be omitted.

The control unit 200 may further include a three-dimensional model generation unit 240 for generating image data acquired by the scan unit 100 into a three-dimensional model. In order to generate the three-dimensional model, the image data may be acquired through structured light or the like to include depth information of an object. The three-dimensional model may include at least one voxel. At the time of generating the three-dimensional model from the image data, voxels constituting the three-dimensional model may display caries expression values only in regions which the caries expression values overlap. Accordingly, there is an advantage in that the user can easily identify the location, angle, size, etc. of caries in the three-dimensional model, and can provide appropriate treatment to the patient.

The image processing apparatus according to the present disclosure may include the display unit 300 for three-dimensionally displaying the analysis result of the control unit 200 described above. The display unit 300 may display image data, or image data that has been overlapped by a mask. Alternatively, the display unit 300 may display a three-dimensional model and a caries expression value which a voxel of the three-dimensional model has, or may display a three-dimensional model and a caries expression value of a three-dimensional mask mapped on the three-dimensional model together. Accordingly, the user does not need to subjectively analyze the inside of the oral cavity of the patient or the generated three-dimensional model with the naked eye. As described above, with respect to the inside of the patient's oral cavity, the presence or absence of caries and/or a caries class may be objectively determined using artificial intelligence and visually displayed, thereby enabling the user to provide rapid and objective treatment to the patient.

The above description has been made merely for the purpose of illustrating the technical idea of the present disclosure, and those skilled in the art, to which the present disclosure belongs, will understand that various modifications and changes can be made without departing from the essential characteristics of the present disclosure.

Therefore, the embodiments described in the present disclosure are not intended to limit the technical idea of the present disclosure, but are intended to describe the technical idea of the present disclosure, and the scope of the technical idea of the present disclosure is not limited by these embodiments. The protection scope of the present disclosure shall be construed on the basis of the accompanying claims, in such a manner that all of the technical ideas included within the scope equivalent to the claims belong to the present disclosure.

INDUSTRIAL APPLICABILITY

The present disclosure provides an image processing method and an image processing apparatus, wherein in order to easily identify a patient's dental caries, image data is acquired by scanning an object, dental caries is determined from the image data, and the image data, from which the caries has been determined, is displayed in a three-dimensional manner.

What is claimed is:

1. An image processing method comprising:
- acquiring two-dimensional image data of visible light by scanning an object comprising a tooth;
- generating a mask region in the two-dimensional image data upon determining caries of the tooth through two-dimensional image data by using artificial intelligence;
- mapping caries expression values to the mask region of the two-dimensional image data;
- generating a three-dimensional model of an oral cavity surface including at least one voxel from the two-dimensional image data in which the caries expression values are mapped, the three-dimensional model expressing color and shape of the object in a three-dimensional manner; and
- displaying the caries expression values on the three-dimensional model,
- wherein at least part of voxel among the at least one voxel constituting the three-dimensional model displays the caries expression values only in portions where the caries expression values are mapped in the two-dimensional image data.

2. The image processing method of claim 1, wherein generating the three-dimensional model of the oral cavity surface from the two-dimensional image data comprises:
- dividing the two-dimensional image data into at least one large region;
- determining caries for each large region; and
- a step of generating the three-dimensional model from the two-dimensional image data in which the caries has been determined.

3. The image processing method of claim 2, wherein the large region is a superpixel comprising at least one small region.

4. The image processing method of claim 2, wherein dividing the two-dimensional image data into the at least one large region comprises:
- generating multiple large regions by dividing the two-dimensional image data;
- comparing characteristic values between the multiple large regions; and
- adjusting a boundary between the large regions, based on the comparison of the characteristic values.

5. The image processing method of claim 4, wherein the characteristic values are color information acquired from the two-dimensional image data.

6. The image processing method of claim 2, wherein determining the caries for each large region comprises:
- determining presence or absence of caries for each large region of the two-dimensional image data; and
- wherein generating mask region in the two-dimensional image data upon determining caries of the tooth comprises:

generating a mask comprising the mask region, based on the determined presence or absence of caries.

7. The image processing method of claim 6, wherein the caries expression value is at least one of a predetermined color or a predetermined pattern.

8. The image processing method of claim 6, wherein the mask to which the caries expression value is mapped overlaps the two-dimensional image data.

9. The image processing method of claim 8, wherein the two-dimensional image data overlapped with the mask is generated as the three-dimensional model, and the caries expression value is displayed on the three-dimensional model.

10. The image processing method of claim 2, wherein determining the caries for each large region comprises:

determining a caries class for each large region of the two-dimensional image data according to preconfigured criteria;

wherein generating mask region in the two-dimensional image data upon determining caries of the tooth comprises:

generating a mask comprising the mask region, based on the determined caries class; and wherein mapping caries expression values to the mask region of the two-dimensional image data comprises:

mapping a caries expression value corresponding to the caries class to the mask region.

11. The image processing method of claim 10, wherein the caries expression value has a different color or pattern for each caries class.

12. An image processing apparatus comprising:

a scanner configured to acquire two-dimensional image data of visible light by scanning an object comprising a tooth;

a control unit configured to:

generate mask region in the two-dimensional image data upon determining caries of the tooth through two-dimensional image data by using artificial intelligence;

map caries expression values to the mask region of the two-dimensional image; and generate a three-dimensional model of an oral cavity surface including at least one voxel from the two-dimensional image data in which the caries expression values are mapped, the three-dimensional model expressing color and shape of the object in a three-dimensional manner; and a display unit configured to display the caries expression values on a three-dimensional model which expresses color and shape of the object in a three-dimensional manner, and is generated from the two-dimensional image data in which the caries expression values are mapped, wherein at least part of voxel among the at least one voxel constituting the three- dimensional model displays the caries expression values only in portions where the caries expression values are mapped in the two-dimensional image data.

13. The image processing apparatus of claim 12, wherein the control unit is configured to:

divide the two-dimensional image data into at least one large region; and determine caries for each large region.

14. The image processing apparatus of claim 13, wherein the large region is a superpixel comprising at least one small region.

15. The image processing apparatus of claim 13, wherein the control unit is configured to:

(1) generate multiple large regions by dividing the two-dimensional image data;

(2) compare characteristic values of the multiple large regions; and (3) adjust a boundary between the large regions, based on the comparison of the characteristic values.

16. The image processing apparatus of claim 15, wherein the characteristic values are color information acquired from the two-dimensional image data.

17. The image processing apparatus of claim 13, wherein the control unit is configured to determine presence or absence of caries for each large region of the two-dimensional image data.

18. The image processing apparatus of claim 13, wherein the control unit is configured to determine a caries class for each large region of the two-dimensional image data.

19. The image processing apparatus of claim 13, wherein the control unit further is configured to:

generate a mask comprising the mask region as a result of determining presence or absence of caries or a caries class for each large region, and map a caries expression value corresponding to the presence or absence of caries or the caries class to the mask region so that the mask overlaps the two-dimensional image data.

20. The image processing apparatus of claim 19, wherein the control unit further comprises a three-dimensional model generation unit configured to generate the two-dimensional image data, which is overlapped by the mask, as the three-dimensional model, and wherein the display unit is configured to display the three-dimensional model and the caries expression value overlapping the three-dimensional model together.

* * * * *